US00PP09278P

United States Patent [19]

Trees

[11] Patent Number: Plant 9,278

[45] Date of Patent: Sep. 5, 1995

[54] NEW GUINEA IMPATIENS NAMED 'LIGHT LAVENDER II'

[75] Inventor: Scott C. Trees, Arroyo Grande, Calif.

[73] Assignee: Geo J. Ball, Inc., West Chicago, Ill.

[21] Appl. No.: 337,530

[22] Filed: Nov. 8, 1994

[51] Int. Cl.[6] ..... A01H 5/00

[52] U.S. Cl. ..... Plt./87.6

[58] Field of Search ..... Plt. 87.6

*Primary Examiner*—James R. Feyrer

*Attorney, Agent, or Firm*—Burns, Doane, Swecker & Mathis

[57] ABSTRACT

A new and distinct New Guinea Impatiens cultivar named Light Lavender II is provided. This new cultivar was the result of a controlled breeding program wherein the Antares cultivar (non-patented in the United States) was pollinated by a plant designated 4050-15 (non-patented in the United States). The new cultivar forms large light lavender flowers with a white eye which display an iridescent appearance, solid medium green foliage, strong basal branching, and a medium growth habit. The new cultivar can be readily distinguished from the Light Lavender cultivar (U.S. Plant Pat. No. 7,671).

1 Drawing Sheet

SUMMARY OF THE INVENTION

The present invention comprises a new and distinctive Impatiens plant, botanically known as New Guinea Impatiens, and hereinafter referred to by the cultivar name Light Lavender II.

The new cultivar is the product of a planned breeding program. More specifically, the breeding program which resulted in the production of the new cultivar was carried out in a controlled environement during 1992 at Arroyo Grande, Calif., U.S.A. The female parent (i.e., the seed parent) was the Antares cultivar (non-patented in the United States) which freely exhibits medium lavender flowers, dark green foliage, and a compact mounded growth habit. The male parent (i.e., the pollen parent) was a plant designated 4050-15 (non-patented in the United States) which exhibits bi-color dark and medium-purple flowers, bronze foliage and a vigorous mounded growth habit. The parentage of the, new cultivar can be summarized as follows:

ANTARES×4050-15.

The seeds resulting from the above pollination were sown and plantlets were obtained which were physically and biologically different from each other. Selective study resulted in the identification of a single plant of the new cultivar. This plant had large light lavender flowers and initially was designated BFP-342.

It was found that the new cultivar of the present invention:

(a) exhibits attractive large light lavender flowers with a white eye,
(b) forms medium green foliage,
(c) exhibits a good basal branching character, and
(d) exhibits a medium upright growth habit.

Asexual reproduction of the new cultivar by terminal or stem cuttings taken during 1993, at Arroyo Grande, Calif., U.S.A. has demonstrated that the characteristics of the new cultivar as herein described are firmly fixed and are retained through successive generations of such asexual propagation.

The Light Lavender II cultivar has not been observed under all possible environmental conditions to date. Accordingly, it is possible that the phenotype may vary somewhat with variations in the environment, such as temperature, light intensity, and day length.

When the new cultivar of the present invention is compared to the Light Lavender cultivar (U.S. Plant Pat. No. 6,671), it is found that the new variety possesses larger flowers which exhibit a truer lavender color, non-variegated foliage, better basal branching, and a more moderate growth habit.

When plant material of the Light Lavender II cultivar is subjected to standard random amplified polymorphic DNA marker analysis (RAPD) using polymerase chain reaction (PCR) and a known unique set of DNA primers, it is found to exhibit a different fingerprint map when compared to that of the Light Lavender cultivar which confirms its genetic distinctiveness.

Plants of the new cultivar will be marketed under the Celebration trademark by Geo. J. Ball, Inc.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at West Chicago, Ill., U.S.A.

DETAILED DESCRIPTION

The chart used in the identification of colors described herein is the R.H.S. Colour Chart of The Royal Horticultural Society, London, England. The color values were determined during the third week of July, 1994. The readings were taken between 10:00 and 11:00 a.m. under 2,000 footcandles of light at West Chicago, Ill., U.S.A. The plants were produced from cuttings taken from stock plants of the new cultivar and were grown under greenhouse conditions comparable to those used in commercial practice while utilizing a soilless growth medium and maintaining temperatures of approximately 72° F. during the day and approximately 65° F. during the night.

Propagation:

*Type cutting.*—Terminal tip.

*Time to initiate roots.*—Approximately 14 to 21 days with the shorter times generally being experienced in the summer and the longer times in the winter.

*Rooting habit.*—Fibrous, and branching.

Plant description:

*Form.*—Basal branching.

*Habit of growth.*—Medium upright mounded. A mature plant commonly measures approximately 23 to 26 cm. in height and approximately 26 to 32 cm. in width.

*Foliage.*—The configuration is narrow and lanceolate. The leaves of the new cultivar measure approximately 10.5 cm. in length × approximately 3.2 cm. in width compared to approximately 8.0 cm. in length × 4.0 cm. in width for the Light Lavender cultivar. The foliage of new cultivar is Yellow-Green Group 147A (adaxial); Yellow-Green Group 147B (abaxial). This compares to Green Group 137A with variegation of Yellow Group 3B and venation of Red Group 55C (adaxial), and Green Group 138B (abaxial) for the Light Lavender cultivar. The stem coloration is Yellow-Green Group 145B for both the new cultivar and the Light Lavender cultivars.

Flower description:

*Flower habit.*—Freely flowering.

*Natural Flowering Season.*—Throughout the year in a greenhouse environment.

*Flowers Borne.*—Above foliage, arising from leaf axils.

*Flower color.*—Purple-Violet Group 81C with attachment points of White Group 155 D (adaxial); and Purple Group 75B (abaxial). This can be compared to Purple Group 77B (adaxial) and Purple Group 75B (abaxial) for the Light Lavender cultivar.

*Quantity of flowers.*—Approximately 7 to 12 per branch compared to approximately 8 to 10 per branch for the Light Lavender cultivar.

*Number of petals.*—Five.

*Flower size.*—Approximately 5.8 to 6.4 cm. in length and approximately 5.6 to 6.0 cm. in width. This can be compared to approximately 5.3 to 5.7 cm. in length and approximately 4.9 to 5.2 cm. in width for the Light Lavender cultivar.

*Nectary length.*—Approximately 6.6 cm. which can be compared to approximately 6.4 cm. for the Light Lavender cultivar.

*Nectary color.*—Yellow-Green Group 145B for both new cultivar and the Light Lavender cultivar.

*Reproductive organs.*—The anthers are fused together forming one organ that surrounds the pistil. Generally the anthers shed pollen prior to the stigma becoming receptive. The pollen color is Yellow Group 12D compared to Yellow Group 11C for the Light Lavender cultivar. The stigma color is Yellow-Green Group 154D for both the new cultivar and the Light Lavender cultivar. The ovary color is Yellow-Green Group 144C for the new cultivar compared to Green Group 143C for the Light Lavender cultivar.

I claim:

1. A new and distinct of New Guinea Impatiens named Light Lavender II, substantially as herein shown and described, which:

(a) exhibits attractive, large light lavender flowers with a white eye,
(b) forms medium green foliage,
(c) exhibits a good basal branching character, and
(d) exhibits a medium upright growth habit.

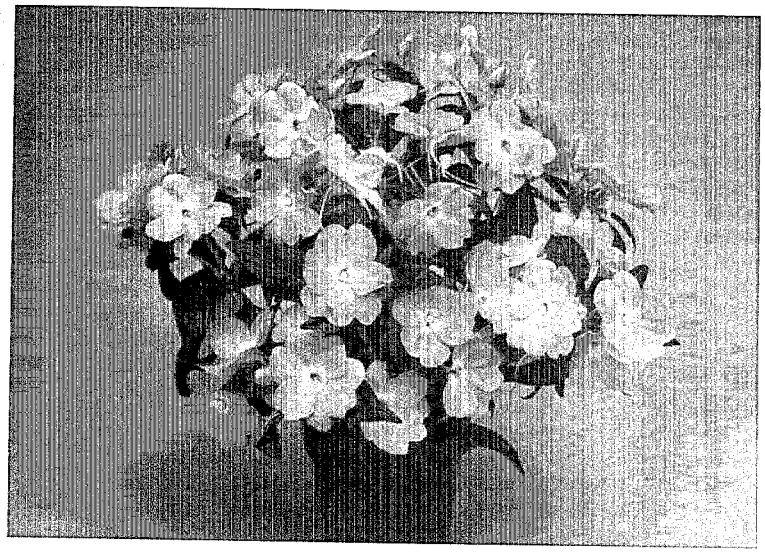

* * * * *